United States Patent
Clawson et al.

[11] Patent Number: 6,105,576
[45] Date of Patent: Aug. 22, 2000

[54] APPARATUS FOR TREATING RESPIRATORY GASES INCLUDING LIQUID TRAP

[75] Inventors: Burrell E. Clawson, Newport Beach, Calif.; James Weigl, Las Vegas, Nev.

[73] Assignee: Enternet Medical, Inc., Las Vegas, Nev.

[21] Appl. No.: 09/172,054

[22] Filed: Oct. 14, 1998

[51] Int. Cl.$^7$ ...................................................... A62B 7/10
[52] U.S. Cl. .................. 128/205.12; 128/201.13
[58] Field of Search ......................... 128/205.12, 203.25, 128/203.26, 203.27, 204.13, 204.17, 911, 201.13

[56] References Cited

U.S. PATENT DOCUMENTS

| | | |
|---|---|---|
| 3,721,238 | 3/1973 | Wise et al. . |
| 3,747,598 | 7/1973 | Cowans . |
| 3,782,081 | 1/1974 | Munters . |
| 3,932,153 | 1/1976 | Byrns . |
| 4,036,616 | 7/1977 | Byrns . |
| 4,040,804 | 8/1977 | Harrison . |
| 4,063,913 | 12/1977 | Kippel et al. ............................... 55/274 |
| 4,090,513 | 5/1978 | Togawa . |
| 4,108,172 | 8/1978 | Moore, Jr. . |
| 4,133,656 | 1/1979 | Kippel et al. . |
| 4,148,732 | 4/1979 | Burrow et al. . |
| 4,168,706 | 9/1979 | Lovell . |
| 4,171,962 | 10/1979 | Kippel et al. . |
| 4,172,709 | 10/1979 | Kippel et al. . |
| 4,181,511 | 1/1980 | Kippel et al. . |
| 4,181,512 | 1/1980 | Kippel et al. . |
| 4,200,094 | 4/1980 | Gedeon et al. . |
| 4,224,939 | 9/1980 | Lang . |
| 4,297,117 | 10/1981 | Holter et al. . |
| 4,327,717 | 5/1982 | Oetjen et al. ...................... 128/201.13 |
| 4,360,018 | 11/1982 | Choksi . |
| 4,367,734 | 1/1983 | Benthin . |
| 4,458,679 | 7/1984 | Ward . |
| 4,516,573 | 5/1985 | Gedeon . |
| 4,597,917 | 7/1986 | Lunsford . |
| 4,707,167 | 11/1987 | Saito et al. . |
| 4,771,770 | 9/1988 | Artemenko et al. . |
| 4,829,997 | 5/1989 | Douwens et al. . |
| 5,016,628 | 5/1991 | Lambert . |
| 5,022,394 | 6/1991 | Chmielinski . |
| 5,035,236 | 7/1991 | Kanegaonkar . |
| 5,038,767 | 8/1991 | Jumpertz . |
| 5,109,471 | 4/1992 | Lang . |
| 5,172,686 | 12/1992 | Anthony . |
| 5,195,527 | 3/1993 | Hicks . |
| 5,213,096 | 5/1993 | Kihlberg et al. . |
| 5,228,435 | 7/1993 | Smith . |
| 5,230,727 | 7/1993 | Pound et al. . |

(List continued on next page.)

FOREIGN PATENT DOCUMENTS

| | | |
|---|---|---|
| 2267840 | 12/1993 | United Kingdom . |
| 2322568 | 9/1998 | United Kingdom . |

*Primary Examiner*—Aaron J. Lewis
*Assistant Examiner*—Teena Mitchell
*Attorney, Agent, or Firm*—Stout, Uxa, Buyan & Mullins, LLP; Frank J. Uxa

[57] ABSTRACT

Apparatus for treating respiratory gases include a housing having an inlet adapted for connection to a tracheal tube device and an outlet adapted for connection to a tube for passing respiratory gases; and a liquid trap chamber positioned between the inlet and the outlet and adapted to receive and hold liquid passed from outside the housing through the inlet or through the outlet. For example, saline or other aqueous liquid which is passed to the patient from outside the housing to loosen and/or remove mucous secretions in the patient can inadvertently slosh back toward the housing. The liquid trap chamber is positioned and adapted to collect and hold such liquid and prevent such liquid from passing further into the housing, for example, to contact and block a filter element located in the housing. An outlet liquid trap chamber is effective to prevent condensed water from a humidifier in a respiratory gas circuit from contacting and detrimentally affecting a filter in the circuit.

20 Claims, 3 Drawing Sheets

U.S. PATENT DOCUMENTS

| | | |
|---|---|---|
| 5,255,674 | 10/1993 | Oftedal et al. . |
| 5,320,096 | 6/1994 | Hans . |
| 5,337,739 | 8/1994 | Lehman . |
| 5,360,002 | 11/1994 | Smith . |
| 5,383,447 | 1/1995 | Lang . |
| 5,386,825 | 2/1995 | Bates . |
| 5,390,668 | 2/1995 | Lehman . |
| 5,435,298 | 7/1995 | Anthony . |
| 5,435,299 | 7/1995 | Langman . |
| 5,460,172 | 10/1995 | Eckerbom et al. . |
| 5,462,048 | 10/1995 | Lambert et al. . |
| 5,468,451 | 11/1995 | Gedeon . |
| 5,482,031 | 1/1996 | Lambert . |
| 5,487,382 | 1/1996 | Bezicot . |
| 5,505,768 | 4/1996 | Altadonna . |
| 5,546,930 | 8/1996 | Wikefeldt . |
| 5,558,088 | 9/1996 | Smith . |
| 5,570,684 | 11/1996 | Behr . |
| 5,577,494 | 11/1996 | Kuypers et al. . |
| 5,590,644 | 1/1997 | Rosenkoetter ............ 128/201.13 |
| 5,592,933 | 1/1997 | Zucchi ............ 128/201.13 |
| 5,647,344 | 7/1997 | Turnbull . |
| 5,738,091 | 4/1998 | Kee et al. ............ 128/205.12 |
| 5,829,428 | 11/1998 | Walters et al. ............ 128/200.24 |
| 5,901,705 | 5/1999 | Leagre ............ 128/207.14 |
| 5,906,201 | 5/1999 | Nilson ............ 128/203.16 |

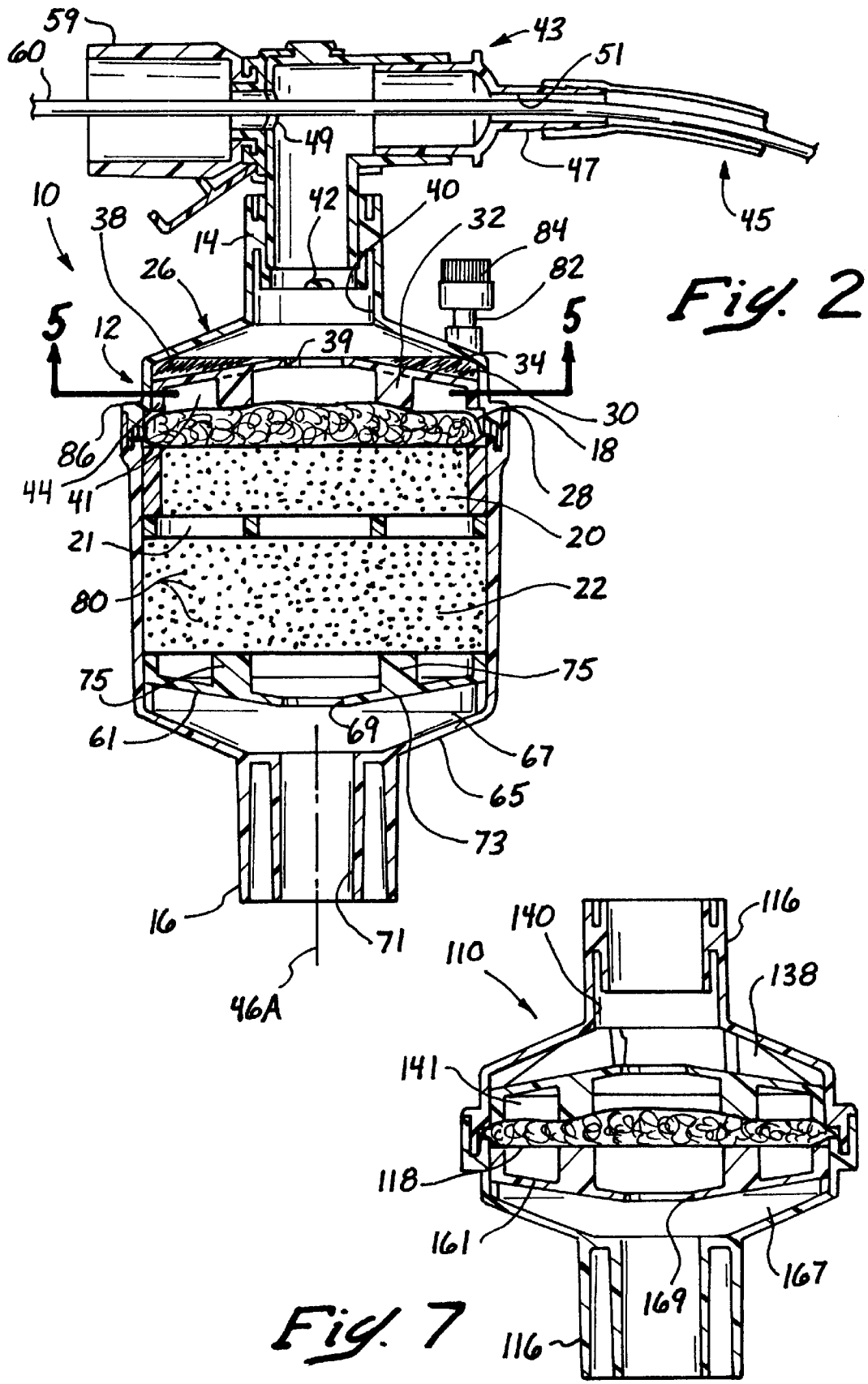

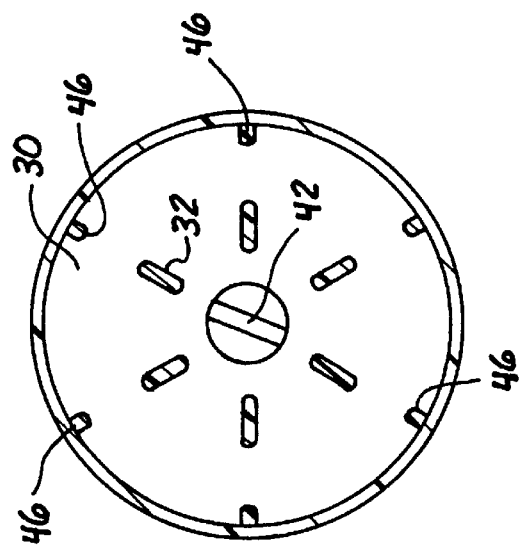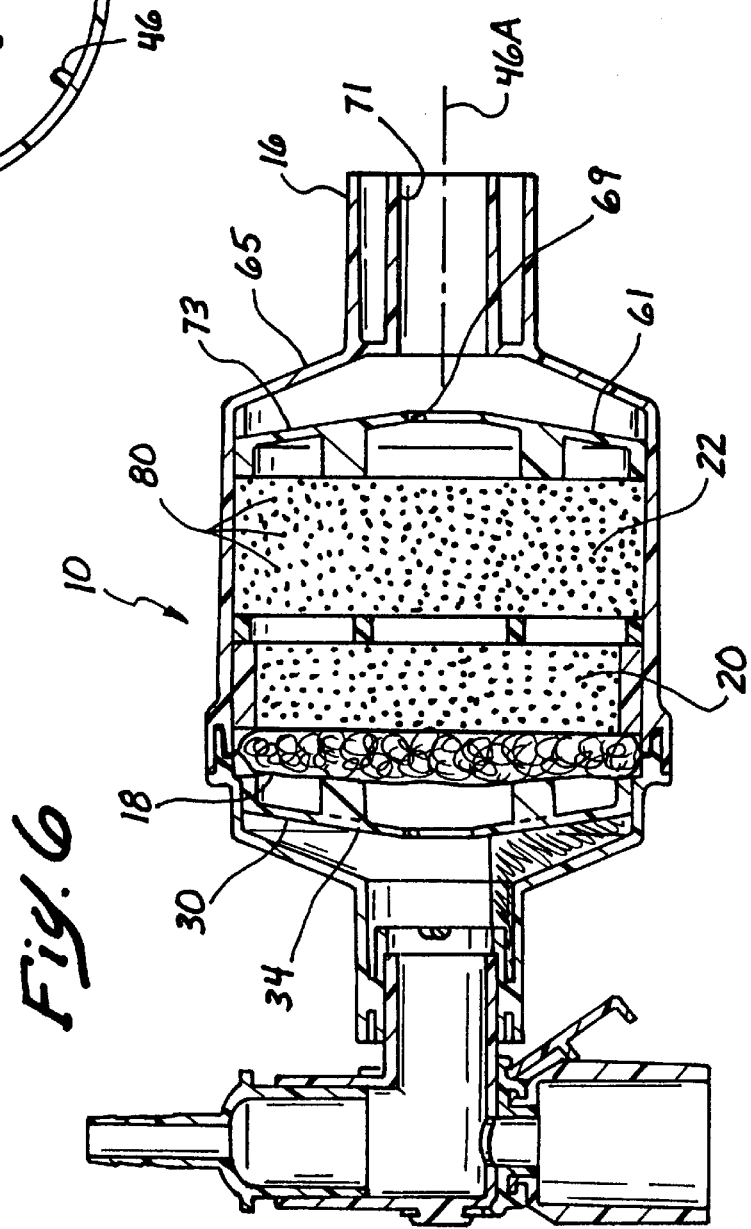

APPARATUS FOR TREATING RESPIRATORY GASES INCLUDING LIQUID TRAP

BACKGROUND OF THE INVENTION

The present invention relates to apparatus useful for treating respiratory gases. More particularly, the invention relates to such apparatus which include liquid traps which preferably are effective to protect one or more components of the apparatus from being contaminated by liquid passed to the apparatus.

During surgery and other medical procedures, a patient is frequently connected to an anesthesia machine or ventilator to provide respiratory gases to the patient. The respiratory gases passed to the patient are advantageously filtered, heated and/or humidified so that the gases entering the patient are of a suitable quality, temperature and humidity so as not to adversely impact the patient. Heat and moisture exchangers (HMEs) are often used to provide heat and humidity to the respiratory gases entering the patient. Typically, these HMEs are located so that respiratory gases from the patient pass through a tracheal tube into the HME, often including a fibrous or other gas permeable material, which accumulates or collects heat and moisture from the exhaled gases. A filter element, for example, an antimicrobial filter element, is often located in the HME to filter respiratory gases passing through the HME. During the inhaling of respiratory gases, for example, from a respiratory ventilator machine, the HME provides both heat and moisture to these respiratory gases prior to the gases entering the patient. Over a period of time, the HME is effective to maintain a certain level of temperature and humidity in the respiratory gases entering the patient.

Although such HMEs do perform effectively to provide at least some of the useful heat and humidity needed for respiratory gases under normal or steady state conditions, additional, needed treatments for the patient may cause adverse effects to the HMEs. One example of such an additional treatment is the use of saline or other aqueous liquids to loosen mucous secretions in the trachea of the patient. Mucous build-up is of particular concern in situations when the patient is an infant or neonate and/or in long term, for example, about six (6) hours or longer, use of a ventilator. Saline lavage is often used to counter such mucous build-up. Thus, saline or other aqueous solution is injected through a suction catheter which is inserted inside the tracheal tube to loosen mucous secretions in the trachea. If the clinician accidentally gets the aqueous solution sloshing back with an exhaled breath or does not suction it correctly in a timely manner, the liquid can fill up or block a good portion of the flow area of the HME and/or the HME's filter element, thereby drastically increasing the pressure required to pass respiratory gases back and forth. In this situation, the HME filter or entire HME may have to be replaced in order to effectively allow respiratory gases to pass to and from the patient. Such replacement can be disruptive and/or harmful to the patient and/or can cause additional clinician stress.

Respiratory gas circuits can include a humidifier and a filter located between the patient and the humidifier. Such circuits are of particular value in treating infants and neonates, for example, with lung volumes on the order of about 10 cubic centimeters. However, liquid water can condense in the tubing from the humidifier and be "blown" or carried to the filter, where such liquid can cause increased pressure drop, disadvantageously making for more difficult respiration.

It would be advantageous to provide apparatus by which respiratory gases can be effectively and reliably treated and which can be protected against liquid material interfering with such treatment and/or causing problems with the respiration of the patient.

SUMMARY OF THE INVENTION

New apparatus for treating respiratory gases, and for protecting such apparatus from liquid passed toward such apparatus, have been discovered. The present invention provides one or more liquid traps effective to separate or segregate liquid, for example, liquid being passed toward an HME or filter included in a system used to provide respiratory gas support to the patient. Such separation or segregation is effective to protect one or more components, for example, an antimicrobial filter element, a fibrous or other gas permeable material and the like, in the HME or filter from being saturated or otherwise blocked with such liquid. The present apparatus are straightforward in construction, easy and relatively inexpensive to manufacture and use and provide effective results without adversely impacting either the HME or the patient receiving respiratory gas support.

Generally, the present invention is directed to apparatus for treating or modifying respiratory gases. Such apparatus comprise a housing and a liquid trap chambers. The housing has an inlet adapted for connection to a tracheal tube device and an outlet adapted for connection to a tube for passing respiratory gases, for example, from a ventilator. The inlet and the outlet are positioned so that respiratory gases passing through the housing pass therebetween. In one embodiment, a liquid trap chamber is positioned between the inlet and the outlet and is adapted to receive and hold liquid passed from outside the housing through the inlet, for example, from the trachea of the patient receiving respiratory gas support from a system including the apparatus. Alternately, a liquid trap chamber is positioned between the inlet and the outlet and is adapted to receive and hold liquid passed from outside the housing through the outlet, for example, from a humidifier or other device included in the patient's respiratory gas support system. In one very useful embodiment, the apparatus includes two liquid trap chambers, one protecting the inlet side of the apparatus and the other protecting the outlet side of the apparatus.

The present invention is particularly applicable in instances in which the housing includes a treatment chamber located between the inlet and the outlet. The treatment chamber contains a treatment component adapted to provide a benefit to the respiratory gases passing through the housing. The liquid trap chamber preferably is positioned to inhibit liquid passed from outside the housing through the inlet or the outlet from entering the treatment chamber or from coming into contact with the treatment component.

The treatment component located in the treatment chamber may be any material or combination of materials effective to provide a benefit to the respiratory gases being passed through the housing. Examples of useful treatment components include: (1) a filter element, e.g., an antimicrobial filter element, adapted to filter respiratory gases passing through the housing; (2) a gas permeable member adapted to exchange heat and moisture with respiratory gases passing through the housing; (3) a generating material adapted to generate water available to humidify respiratory gases passing through the housing; (4) a hygroscopic component adapted to generate heat available to heat respiratory gases passing through the housing, and the like and combinations thereof.

In a particularly useful embodiment, the present apparatus further comprise a fitting adapted to be coupled to the inlet of the housing and to the tracheal tube device. This fitting includes a port through which liquid may be passed into the tracheal tube device and, thus, to the trachea of the patient. For example, a suction catheter may be passed through the port of the fitting into the tracheal tube device. Saline or other aqueous liquid is passed through the suction catheter into the trachea of the patient, for example, to loosen and/or aid in the removal of mucous secretions from the patient.

As noted above, in one embodiment the liquid trap chamber is adapted and positioned to prevent liquid passing through the inlet of the housing from outside the housing, for example, from the trachea of the patient, from entering into the treatment chamber of the apparatus.

In a useful embodiment, the housing includes an inlet portion which includes both the inlet and a liquid trap chamber and/or an outlet portion which includes both the outlet and a liquid trap chamber. The inlet portion and/or outlet portion may be adapted to be decoupled from the remainder of the housing. If a liquid trap chamber becomes filled or otherwise includes a sufficient amount of liquid, a suction catheter or like implement can be utilized to remove the liquid from the trap chamber, for example, after the housing is oriented to cause the liquid to move to a position where it can be removed by suction. In this manner, the treatment chamber of the housing, and the component or components included therein, remain unaffected by the liquid which is removed from the liquid trap chamber. Also, the inlet portion, or the outlet portion, of the housing may be adapted to hold the filter element.

The housing may include a port through which liquid in the liquid trap chamber can be removed. For example, the port, which is normally closed with a cap, can be subjected to suction so as to remove the liquid located in the liquid trap chamber. The port can be in fluid communication with a continuous small flow suction tube to remove the liquid.

Although any suitable construction can be employed to provide the liquid trap chamber, in one particularly useful embodiment, the liquid trap chamber is defined by the housing and a baffle spaced apart from the inlet or the outlet. The inlet, or the outlet, preferably includes an opening having a first open cross-sectional area through which respiratory gases pass. The baffle has an opening having a second open cross-sectional area which may be smaller than the first open cross-sectional area. The size of the baffle opening may vary and is dependent, for example, on the pressure drop requirements of each specific application. This combination of openings is particularly useful in causing the liquid passing through the inlet, or the outlet, to be collected in the liquid trap chamber, rather than passing through the baffle into the treatment chamber.

In a particularly useful embodiment, the inlet, or the outlet, includes a flow diverter element located in the inlet opening, or the outlet opening, respectively. This flow diverter element is adapted to divert liquid from outside the housing through the inlet from passing through the opening in the baffle. Such flow diverter element, preferably in combination with a relatively small opening in the baffle, as described herein, effectively causes the liquid to be collected in the liquid trap chamber.

The liquid trap chamber preferably is configured to inhibit such liquid from entering the treatment chamber, irrespective of the orientation of the housing, for example, irrespective or regardless of the relative orientation of the inlet and the outlet. For example, the configuration of the liquid trap chamber preferably is such that the liquid being held therein remains in the chamber and/or is prevented from entering the treatment chamber whether the apparatus is oriented vertically, that is with the inlet directly above the outlet, or whether the apparatus is oriented horizontally, that is with the inlet and outlet being at substantially the same horizontal level.

This feature is advantageous in that the liquid being held in the liquid trap chamber remains separated from the remainder of the housing, for example, the treatment chamber of the housing, regardless of the orientation of the apparatus. The apparatus may be required to be oriented in various directions for other reasons to facilitate the care of the patient whose respiration is being supported by a system including the apparatus.

The baffle preferably is adapted to be secured to the housing.

In another broad aspect of the present invention, methods for providing respiratory gases to a human or animal are provided. These methods comprise providing an apparatus including a housing having an inlet in fluid communication with a tracheal tube device inserted in the trachea of the human or animal and an outlet connected to a tube for passing respiratory gases to and from the human or animal. The inlet and the outlet are positioned so that respiratory gases passing through the housing pass therebetween. In addition, the apparatus includes a liquid trap chamber positioned between the inlet and the outlet and adapted to receive and hold liquid passed from outside the housing through the inlet or the outlet. Apparatus as described elsewhere herein may be used in accordance with the present methods.

The present methods further include using such apparatus to provide respiratory gases to the human or animal.

In a particularly useful embodiment the present methods further comprise passing aqueous liquid to the human or animal through the tracheal tube device, for example, through a suction catheter as described elsewhere herein. The present methods are particularly useful when aqueous liquid is passed from the trachea of the human or animal toward the housing. In this situation, such aqueous liquid is passed from the trachea to the liquid trap chamber thereby preventing contamination by such liquid of the other component or components of the apparatus.

Commonly assigned U.S. patent applications Ser. No. 09/113,229, filed Jul. 10, 1998 and Ser. No. 09/113,649, filed Jul. 10, 1998, disclose additional features which can be used in combination with the present apparatus and methods. The disclosure of each of these applications, in its entirety, is incorporated by reference herein.

Each individual feature and each combination of two or more features described herein are included within the scope of the present invention provided that the features included in the combination are not mutually inconsistent.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 2 is a front view, partly in cross section, of an embodiment of an apparatus in accordance with the present invention.

FIG. 5 is a view taken generally along lines 5—5 of FIG. 2.

FIG. 6 is a front view, in cross-section of the embodiment of the apparatus in FIG. 2 positioned in a substantially horizontal orientation.

FIG. 7 is a front view, in cross section, of an alternate embodiment of an apparatus in accordance with the present invention.

DETAILED DESCRIPTION OF THE DRAWINGS

Figure 1:
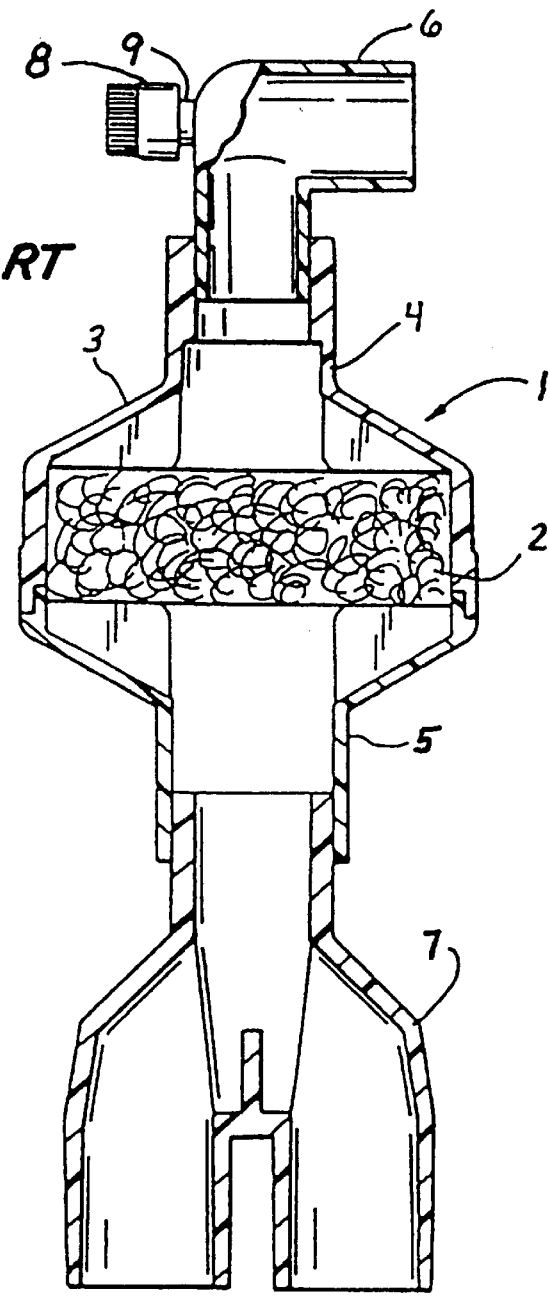
FIG. 1 is a front side view, partly in cross section of a prior art device used to exchange heat and moisture with respiratory gases.

With reference to FIG. 1, an example of a commercially available HME unit, shown generally at 1, includes a heat and moisture exchange (HME) member 2 enclosed in a housing 3 including an inlet 4 and an outlet 5. An elbow fitting 6 is connected to the inlet 4 of the housing 3. This elbow fitting 6 is adapted to be connected to a tracheal tube device, not shown.

A manifold 7, adapted to be connected to a device for passing respiratory gases, is connected to the outlet 5 of housing 3.

The HME unit 1 can be employed to provide a saline or other aqueous liquid to the trachea of the patient whose respiration is being supported by a system including the unit. This is done by removing cap 8 from port 9 in elbow fitting 6. A suction catheter (not shown) of conventional construction is passed through port 9 into the tracheal tube device being used in combination with HME unit 1. Often a specifically designed elbow fitting or manifold with a larger port is employed to aid the use of the suction catheter. Saline or other aqueous liquid is passed through the suction catheter into the trachea of the patient to loosen mucous to facilitate respiration. In the ordinary circumstance, the clinician is able to withdraw the aqueous liquid and mucous through the suction catheter. However, if the respiration of the patient is uneven and/or not properly timed by the clinician, the aqueous liquid can slosh from the trachea into elbow fitting 6 and eventually into housing 3. This aqueous liquid contaminates the HME unit 1 and causes additional pressure drop through the HME unit which adversely affects respiration. If this occurs with HME unit 1, substantially the only way to eliminate this problem is to entirely replace the HME unit. This is costly and can result in substantial disruption and trauma to the patient whose respiration is being supported.

An embodiment of the apparatus in accordance with the present invention is shown in FIG. 2. This apparatus, shown generally at 10, includes a housing 12 having an inlet 14 and an outlet 16. Apparatus 10 also includes an antimicrobial filter element 18, generating material 20 and a gas permeable member 22. A space 21 is located between generating material 20 and gas permeable member 22.

The tracheal tube device 45 is connected to the inlet 14 of the apparatus 10 via fitting 43. The outlet 16 of the apparatus 10 is joined or connected to one or more tubes which communicate with an anesthesia machine or a ventilator (not shown) of conventional construction. In this arrangement, the patient is provided with respiratory gases from the anesthesia machine or ventilator through outlet 16. Such gases pass into and through the remainder of the apparatus 10, and through tracheal tube device 45 into the trachea of the patient. Exhaled respiratory gases passed from the trachea through the tracheal tube device 45 and the apparatus 10 and out of the outlet 16 toward the anesthesia machine or ventilator. This cycle is repeated each time the patient inhales and exhales respiratory gases.

Housing 12 includes an inlet portion 26 which includes inlet 14 and an outwardly extending segment 28 to which filter element 18 is secured. A sloped inlet baffle 30 is removably secured to the inlet portion 26. Sloped inlet baffle 30 includes a series of downwardly extending projections 32 which terminate in contact with or in close proximity to filter element 18 and act to facilitate maintaining the filter element in place, as shown in FIG. 2. The sloped surface 34 of inlet baffle 30, together with inlet portion 26 of housing 12 forms an inlet liquid trap chamber 38. Inlet baffle 30 includes a central opening 39 which has a smaller cross-sectional area then does inlet opening 40 of inlet 14. In addition, inlet 14 includes a flow diverter bar 42 which extends substantially across opening 40 and is aligned with opening 39 of baffle 30.

Liquid coming from the patient through fitting 43 turns a 90° (elbow) corner in moving from the fitting 43 to the inlet 14, which causes the liquid to be forced onto the interior walls of inlet portion 26 by virtue of the centrifical force involved. The relatively small size of opening 39 and the sloped surface 34 of inlet baffle 30 effectively prevents liquid from passing through opening 39. This liquid is collected and held in inlet liquid trap chamber 38.

Inlet baffle 30 is secured to inlet portion 26. This is accomplished using a series of pegs 44 which downwardly extend from the periphery of sloping surface 34 and fit onto complimentary projections 46 which extend outwardly from the interior surface of inlet portion 26. Because of the flexibility of pegs 44, the baffle 30 can be relatively easily removed from inlet portion 26. Alternately, the baffle 30 can be permanently secured to the inlet portion 26.

Outlet baffle 61 is positioned near the outlet 16 of housing 12. Outlet baffle 61 is supported in place by a raised bead on the inside wall of the housing. The outlet baffle 61 snaps past this raised bead to be held or supported in place. An outlet liquid trap chamber 67 is defined by the outlet 16, outlet end wall 65 and outlet baffle 61. Central opening 69 in outlet baffle 61 has a smaller cross section than does outlet opening 71. Outlet baffle 61 includes a sloped surface 73 and a series of upwardly extending projections 75 which terminate in contact with or in close proximity to gas permeable member 22 and act to facilitate maintaining the gas permeable member in place, as shown in FIG. 2.

Liquid, for example, condensed water, from outside housing 12, passing through outlet opening 71 passes into outlet water trap chamber 67 and is effectively prevented from passing through opening 69. Thus, such liquid is prevented from coming in contact with the permeable member 22, generating material 20 and filter element 18.

Housing 12 can be made of any suitable material of construction. Preferably, housing 12 is made of polymeric material. The housing 12 is configured or structured so as to minimize the amount of open or dead space above filter element 18 and below gas permeable member 22. This provides for more efficient and effective heat and moisture transfer, for example, relative to commercially available HME unit 1. In addition, the size of apparatus 10 is small relative to the size of HME unit 1. This provides for relative ease in using the apparatus 10 and reduces the amount of space taken up by the apparatus.

Fitting 43 is connected to both inlet 14 and tracheal tube device 45. Tracheal tube device 45 is joined directly to first end 47 of fitting 43. Located directly opposite first end 47 is a second end opening 49 which is substantially aligned with the opening 51 defined by first end 47.

Figure 4:
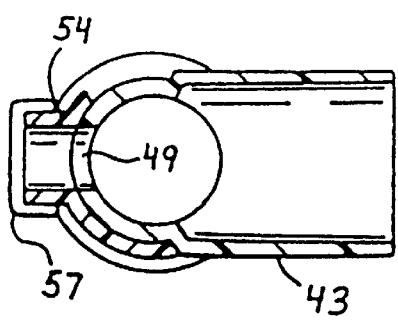
FIG. 4 is a partial top view of the fitting shown in FIG. 2 with a cap covering the port.
Figure 3:
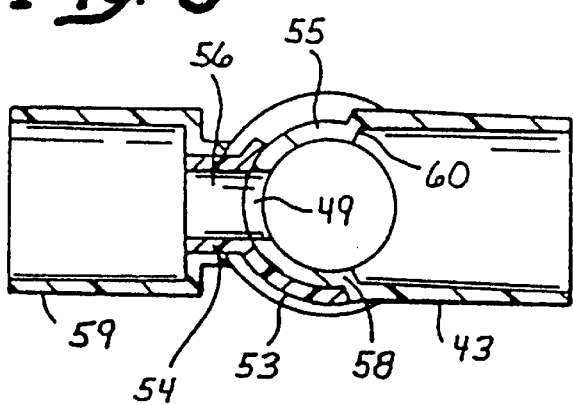
FIG. 3 is a partial top view of the fitting and complimentary adaptor (closure assembly) shown in FIG. 2.

With particular reference to FIG. 3, a rotatable closure element 53 is positioned and carried on the second end 55 of fitting 43. Closure element 53 includes a closure outlet or through port 54. By rotating closure element 53 about second end 55, second end opening 49 can be either opened or closed to the passageway 56 defined by closure outlet 54. In addition, even if second end opening 49 is opened, a cap 57, which is secured to fitting 43, can be placed on closure outlet 54 to cover the through port. This feature is shown in FIG. 4. Rotatable closure element 53 rotates between first stop 58 and second stop 60 on fitting 43. When the closure element 53 is in contact with first stop 58, second end opening 49 is in fluid communication with closure outlet 54. When the closure element 53 is in contact with second stop 60, second opening 49 is out of fluid communication with closure outlet 54.

As shown in FIGS. 2 and 4, second end opening 49 can be opened and in fluid communication with a tube 59 through which a suction catheter 60 can be provided to tracheal tube device 45 and into the trachea of the patient.

A hollow treatment chamber 41 is formed by the housing 12. Located within the treatment chamber 41 and extending substantially across the entire cross-section of the chamber are the antimicrobial filter element 18 which is secured to the inlet portion 26 of the housing 12, a quantity of particulate generating material 20, in particular, particulate carbon dioxide absorbing material, and a gas permeable member 22, in particular a fibrous or cellular member.

Respiratory gases from the patient pass through inlet opening or passage 40 defined by inlet 14, through opening 39 in baffle 30 and into chamber 41. Inlet 14 is part of housing 12. Such respiratory gases pass through filter element 18, generating material 20 and gas permeable member 22 before exiting through opening 69 and outlet opening 71 defined by outlet 16. Outlet 16 is part of housing 12. When respiratory gases are to be inhaled by the patient, such gases pass into apparatus 10 through outlet opening 71, opening 69 into chamber 41, across gas permeable member 22, generating material 20 and filter element 18. This respiratory gas to be inhaled is passed through opening 39 and inlet passage 40 into tracheal tube device 45 and into the trachea of the patient.

The filter element 18, generating material 20 and gas permeable member 22 are all positioned substantially perpendicular to the longitudinal axis 46A of apparatus 10. Thus, the filter element 18, generating material 20 and gas permeable member 22 are all substantially perpendicular to the general direction of flow between the inlet passage 40 and the outlet opening or passage 71.

The filter element 18 may be of any suitable configuration to remove contaminants from the respiratory gas passing therethrough. The filter element 18 should be sufficiently gas permeable so that the respiratory gases passing therethrough result in a relatively reduced, or even minimal pressure differential. The filter element 18 may be chosen from filter material used in conventional respiratory filters or heat and moisture exchangers for respiratory gases, many of which are known and commercially available. The filter element 18 may have antimicrobial activity.

The gas permeable member 22 is selected to provide for both heat and moisture exchange with gases passing through the housing 12. The gas permeable member may be chosen from any suitable material which is effective as a heat and moisture exchanging material and has gas permeability. Examples of useful materials from which gas permeable member 22 can be chosen include such materials which are conventionally used in heat and moisture exchangers for respiratory gases, many of which are well known and commercially available.

The generating material 20, which is located between and adjacent the filter element 18 and the gas permeable member 22, is effective to generate both water and heat, preferably in response to an interaction with carbon dioxide, for example, absorption of and subsequent reaction with carbon dioxide, in the respiratory gas which comes in contact with the generating material. The carbon dioxide generating material making up generating material 22 preferably is in the form of particles which are effective to absorb, or otherwise interact with, carbon dioxide in the respiratory gases. The generating material 20 preferably is sufficiently gas permeable so that respiratory gases passing therethrough result in a substantially reduced, or even in a minimal pressure differential.

In a very useful embodiment, the amount of generating material present is effective to generate only a portion, more preferably a minor portion (that is, no more than about 50%), of the water to humidify respiratory gases passing through the housing. In particular, the amount of generating material present in the housing is effective to generate at least about 5%, more preferably at least about 10%, and still more preferably at least about 15% of the water to humidify respiratory gases passing through the housing. On the other hand, the amount of generating material present in the housing preferably is effective to generate no more than about 50% of the moisture of the water to humidify respiratory gases passing through the housing. Having excessively large amounts generating material present in the housing can result in the respiratory gases passing to the patient having a temperature which is excessively high relative to the requirements of the patient.

Although any suitable component or combinations of components may be useful in generating material 20 to generate moisture and heat, it is preferred that the generating material be that sold by W. R. Grace under the trademark "SODA SORB".

It should be noted that the generating material 20 need not be present or may be replaced by an inert thermal mass and/or another HME element. None of the treating components within housing 12 are essential. The treatment component or components can be selected to fit the needs of any given application.

A hygroscopic material, shown in FIGS. 2 and 6 as particles of calcium chloride 80 coated on or embedded in the gas permeable material 22, is very effective in assisting the apparatus 10 during initial or startup operation. The hygroscopic material 80 comes in contact with water vapor from respiratory gases passing through the housing 12 and produces heat which is available for transfer to the respiratory gases being passed to the patient. As an alternative, the location of the hygroscopic material can be near the outlet 16 of housing 12, for example, as a separate layer of material in proximity to the outlet side of the gas permeable material 22. This location of the hygroscopic material is beneficial in that moisture which interacts with the hygroscopic material to generate heat would, if not so interacted, be removed from the apparatus 10 and become unavailable to the patient. Placing the hygroscopic material near the outlet 16, therefore, provides a substantial benefit to the patient which would otherwise be lost to the patient. A tray-like element may be provided so that respiratory gases passing out of the housing 12 contact the hygroscopic material and interact to generate heat. As respiratory gases move into the housing 12 across the tray-like element, such gases pick up the heat produced by the hygroscopic material and provide warmed respiratory gases to the patient.

The inlet portion 26 of the housing 12 includes a suction port 82 which is normally closed using cap 84. However, if liquid is present in the inlet liquid trap chamber 38, the cap 84 can be removed and a suction tube passed into port 84 so that the liquid in the chamber 38 can be removed. Alternately, port 82 can be placed in fluid communication with a continuous small flow suction tube to remove any liquid in chamber 38.

Inlet portion 26 can be removable from the remainder of housing 12, for example, using a conventional dogging assembly. Thus, a dogging assembly can be arranged and configured so that a peripheral rim surface 86 of inlet portion 26 is provided. This peripheral rim surface 86 is rounded and continuous around the entire periphery of inlet portion 26. This rounded peripheral rim surface 86 is very effective in reducing the risk that the apparatus 10 will snag or otherwise be caught up in the patient, in/her garments and/or other objects used in treating the patient. In turn, this reduces the risk of causing trauma to the patient as a result of the tracheal tube 45 being jousted about because of such snagging, etc.

FIG. 6 illustrates an additional important feature of the present apparatus 10. Thus, in FIG. 6, apparatus 10 is shown oriented in a generally horizontal manner. Thus, the longitudinal axis 46 of apparatus 10 is substantially horizontal. In this orientation, with liquid present in the inlet liquid trap chamber 38, the liquid is again prevented from contacting the filter element 18 since the level of the liquid does not overlap the opening 39 of the sloped baffle 30. Also, liquid present in outlet liquid trap chamber 67 is prevented from contacting gas permeable member 22 since the level of the liquid does not overlap the opening 69 in outlet baffle 61. This configuration is particularly beneficial in that the orientation of the apparatus 10 may be varied over a wide range from vertical (as shown in FIG. 2) to horizontal (as shown in FIG. 6) without the liquid in the liquid trap chambers coming in contact with the components in the treatment chamber 41.

The apparatus 10 functions as follows. The apparatus 10 is connected to the respiratory system of a patient, as described above. As the patient exhales gases, such gases pass through inlet opening 40 and baffle opening 39 into treatment chamber 41. These exhaled gases pass through filter element 18 and are, at least to some extent, purified and contaminants are removed and/or destroyed. The exhaled respiratory gases includes carbon dioxide, at least a portion of which interacts with the generating material 20 as the respiratory gases pass therethrough. This results in a generation of heat and moisture which passes into gas permeable member 22, along with the heat and moisture originally present in the respiratory gases being exhaled by the patient. This heat and moisture is collected by a gas permeable member 22 as the exhaled respiratory gases pass therethrough. The exhaled respiratory gases pass out of the apparatus 10 through opening 69 outlet passage 71.

During the time the patient is inhaling gases, respiratory gases to be inhaled are passed into apparatus 10 through outlet passage 71 and opening 69. The to-be inhaled gases pass through gas permeable member 22 where heat and moisture from the fibrous member are transferred to the respiratory gases to be inhaled. Additional heat and moisture is released to the respiratory gases to be inhaled as the gas is passed through the generating material 20 to provide the desired amount of heat and moisture to such gases. Finally, the respiratory gases to be inhaled pass through the filter element 18 through baffle opening 39 and out of apparatus 10 through inlet passage 40 into the tracheal tube 45 and the trachea of the patient.

This inhale/exhale cycle is continued with the result that the patient is provided with respiratory gases which have a desired degree of heat and humidity so that the patient is not detrimentally affected by respiratory gases which are too dry or too cold.

The inhale/exhale cycle described above occurs with the opening 49 closed and with the suction catheter tube 60 withdrawn from the tracheal tube device 45.

In situations where there is an indication of excessive mucous secretions in the patient's trachea, the suction catheter tube 60 can be placed through opening 49 into the fitting 43 and tracheal tube device 45, as shown in FIG. 2. Saline or aqueous liquid is passed through the suction catheter tube 60 into the trachea of the patient. This aqueous liquid loosens mucous secretions. Suction is applied to the suction catheter tube 60 to remove the saline and mucous from the patient, thereby making his/her respiration substantially easier.

With the suction catheter tube 60 inserted as shown in FIG. 2, the clinician may inadvertently mistime the withdrawal of the saline or other aqueous liquid and mucous from the patient. For example, if the patient is exhaling without suction being drawn, the aqueous liquid/mucous mixture passes up the trachea into the tracheal tube device and into the fitting 43. This mixture passes into and through the inlet passage 40 and collects in the liquid trap chamber 38. This liquid trap chamber 38 effectively prevents the liquid/mucous mixture from contacting the filter element 18 and other components in the chamber 41.

The catheter suction tube 60 is removed from the trachea tube 45. The liquid mixture in the liquid trap chamber 38 can be suctioned out using catheter suction tube 60. Thus, if the clinician sees liquid in chamber 38, he/she can pull the catheter suction tube 60 back to where it enters the fitting 43. The housing 12 is then oriented, e.g., tilted, so that the trapped liquid flows back to the tip of the catheter tube 60 to be suctioned and removed.

Except as expressly described herein, apparatus 110 (FIG. 7) is substantially similar to apparatus 10. Components of apparatus 110 which correspond to components of apparatus 10 are identified by the same reference numerals increased by 100.

The primary difference between apparatus 110 and apparatus 10 has to do with the treatment chamber 141. Specifically, the treatment chamber 141 of apparatus 110 includes filter element 118 but does not include any component corresponding to the generating material 20 and the gas permeable member 22 described previously with regard to apparatus 10.

Apparatus 110 has particular value when used in combination with a respiratory gas circuit including a humidifier. Such respiratory gas circuits are very useful, for example, in treating neonates and infants.

Apparatus 110 can be coupled to a fitting, similar in construction to fitting 43, for providing respiratory gases to the trachea of a patient. Also, apparatus 110 is very effective in preventing liquid from the patient from entering the treatment chamber 141, for example, in a manner similar to that described herein with regard to apparatus 10.

Specifically, liquid, for example, saline expelled from the patient, entering the inlet opening 140 of apparatus 110 is collected and held in inlet water trap chamber 138. Such liquid can be removed from inlet water trap chamber 138, for example, using the techniques described herein with regard to remaining liquid from chamber 38.

In addition, apparatus 110 is designed and configured to prevent liquid, for example, condensed liquid water from a humidifier, passing through the outlet 116 from entering treatment chamber. This liquid water is inhibited from entering treatment chamber 141 by the combination of outlet baffle 161, central opening 169 and outlet water trap chamber 167.

Using apparatus 110, the filter element 118 is protected from being contacted by liquid coming from the outlet 116.

The inclusion of one or more water trap chambers, as described herein, provides benefits to the patient in that his/her respiration can be made easier while maintaining the present apparatus in a highly operable condition. In addition, the clinician treating the patient, for example, operating a suction catheter tube to make the patient's respiration easier, experiences reduced anxiety, for example, since the liquid which may slosh back out of the trachea of the patient is largely prevented from contacting the filter element. In addition, these benefits are achieved in a cost effective manner, thereby helping to reduce the overall cost of treating the patient.

While this invention has been described with respect to various specific examples and embodiments, it is to be understood that the invention is not limited thereto and that it can be variously practiced within the scope of the following claims.

What is claimed is:

1. An apparatus for treating respiratory gases comprising:
    a housing having a first port adapted for connection to a tracheal tube device and a second port adapted for connection to a tube for passing respiratory gases, the first port and the second port being positioned so that respiratory gases passing through the housing pass therebetween; and
    a liquid trap chamber positioned between the first port and the second port and adapted to receive and hold liquid passed from outside the housing through the first port or through the second port.

2. The apparatus of claim 1 which further comprises an additional liquid trap chamber positioned between the first port and the second port and adapted to receive and hold liquid passed from outside the housing through the first port or the second port, provided that only one of the liquid trap chambers is adapted to receive and hold liquid passed through the first port.

3. The apparatus of claim 1 wherein the housing includes a treatment chamber located between the first port and the second port, the treatment chamber contains a treatment component adapted to provide a benefit to the respiratory gases passing through the housing, and the liquid trap chamber being positioned to inhibit liquid passed from outside the housing through the first port or through the second port from entering the treatment chamber.

4. The apparatus of claim 3 wherein the treatment component is selected from the group consisting of: (1) a filter element adapted to filter respiratory gases passing through the housing; (2) a gas permeable member adapted to exchange heat and moisture with respiratory gases passing through the housing; (3) a generating material adapted to generate water available to humidify respiratory gases passing through the housing; (4) a hygroscopic component adapted to generate heat available to heat respiratory gases passing through the housing and (5) combinations thereof.

5. The apparatus of claim 3 wherein the liquid trap chamber is configured to inhibit liquid passed from outside the housing through the first port or the second port from entering the treatment chamber regardless of the orientation of the housing.

6. The apparatus of claim 1 which further comprises a fitting adapted to be coupled to the first port of the housing and to a tracheal tube device, and to include a port through which liquid is passed into a tracheal tube device, and the liquid trap chamber is adapted to receive and hold liquid passed from outside the housing through the first port.

7. The apparatus of claim 6 wherein the baffle is adapted to be secured to the housing.

8. The apparatus of claim 1 wherein the liquid trap chamber is defined by the housing and a baffle spaced apart from the first port or the second port.

9. The apparatus of claim 8, which further comprises a flow diverter element located in the first port opening of the second opening and adapted to divert liquid passing from outside the housing through the first port or the second port, respectively, from passing through an opening in the baffle.

10. The apparatus of claim 1 wherein the liquid trap chamber is sized and positioned to hold liquid passed from outside the housing through the first port or the second port irrespective of the relative orientation of the first port and the second port.

11. A method for providing respiratory gases to a human or animal comprising:
    providing an apparatus including a housing having a first port in fluid communication with a tracheal tube device inserted in a trachea of the human or animal and a second port connected to a tube for passing respiratory gases to and from the human or animal, the first port and the second port being positioned so that respiratory gases passing through the housing pass therebetween, and a liquid trap chamber positioned between the first port and the second port and adapted to receive and hold liquid passed from outside the housing through the first port or through the second port; and
    using the apparatus to provide respiratory gases to the human or animal.

12. The method of claim 11 wherein the apparatus further comprises an additional liquid trap chamber positioned between the first port and the second port and adapted to receive and hold liquid passed from outside the housing through the first port or the second port, provided that only one of the liquid trap chambers is adapted to receive and hold liquid passed through the first port.

13. The method of claim 11 wherein the housing includes a treatment chamber located between the first port and the second port, the treatment chamber contains a treatment component adapted to provide a benefit to the respiratory gases passing through the housing, and the liquid trap chamber being positioned to inhibit liquid passed from outside the housing through the first port or through the second port from entering the treatment chamber.

14. The method of claim 13 wherein the treatment component is selected from the group consisting of: (1) a filter element adapted to filter respiratory gases passing through the housing; (2) a gas permeable member adapted to exchange heat and moisture with respiratory gases passing through the housing; (3) a generating material adapted to generate water available to humidify respiratory gases passing through the housing; (4) a hygroscopic component adapted to generate heat available to heat respiratory gases passing through the housing and (5) combinations thereof.

15. The method of claim 11 wherein the liquid trap chamber is adapted to receive and hold liquid passed from outside the housing through the inlet, and the method further comprises passing aqueous liquid to the human or animal through the tracheal tube device.

16. The method of claim 15 wherein the apparatus further comprises a fitting coupled to the first port of the housing and to the tracheal tube device, and to include a port through which liquid is passed into the tracheal tube device and the method further comprises removing aqueous liquid and mucous from the human or animal through the fitting.

17. The method of claim 15 which further comprises passing aqueous liquid from the tracheal tube device to the liquid trap chamber.

18. The method of claim 17 which further comprises removing the aqueous liquid from the liquid trap chamber.

19. The method of claim 18 wherein the removing step includes suctioning the aqueous liquid from the liquid trap chamber.

20. The method of claim 11 wherein the liquid trap chamber is configured to inhibit liquid passed from outside the housing through the first port or the second port from entering the treatment chamber regardless of the orientation of the housing.

* * * * *